United States Patent
Toy et al.

(10) Patent No.: US 10,994,112 B2
(45) Date of Patent: May 4, 2021

(54) DRUG DELIVERY SYSTEM WITH ELECTROMAGNETIC FIELD GENERATOR

(71) Applicant: AMGEN INC., Thousand Oaks, CA (US)

(72) Inventors: Stephanie Toy, Moorpark, CA (US); Mark Ka Lai Lee, Newbury Park, CA (US); Donald Busby, Thousand Oaks, CA (US); Melissa D. Norton, Santa Clarita, CA (US); Jeffrey Chen, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 331 days.

(21) Appl. No.: 15/039,946

(22) PCT Filed: Feb. 3, 2015

(86) PCT No.: PCT/US2015/014162
§ 371 (c)(1),
(2) Date: May 27, 2016

(87) PCT Pub. No.: WO2015/119906
PCT Pub. Date: Aug. 13, 2015

(65) Prior Publication Data
US 2018/0193623 A1 Jul. 12, 2018

Related U.S. Application Data

(60) Provisional application No. 61/936,125, filed on Feb. 5, 2014.

(51) Int. Cl.
*A61M 37/00* (2006.01)
*A61N 1/04* (2006.01)
*A61N 1/32* (2006.01)

(52) U.S. Cl.
CPC ........ *A61M 37/0015* (2013.01); *A61M 37/00* (2013.01); *A61M 2037/0007* (2013.01);
(Continued)

(58) Field of Classification Search
CPC ...... A61M 37/0015; A61M 2037/0007; A61M 2037/0023; A61M 2037/0061; A61M 2037/0003
See application file for complete search history.

(56) References Cited

U.S. PATENT DOCUMENTS 6,317,630 B1 * 11/2001 Gross .................. A61N 1/30
604/20
6,463,336 B1 10/2002 Mawhinney
(Continued)

FOREIGN PATENT DOCUMENTS

WO  WO-0044437 A1  8/2000
WO  WO-2011053607 A1  5/2011

OTHER PUBLICATIONS

Sullivan, David. MD, et. al. Effect of a Monoclonal Antibody to PCSK9 on Low-Density Lipoprotein Cholesterol Levels in Statin-Intolerant Patients. Dec. 19, 2012. Journal of the American Medical Association. vol. 308, No. 23. 2497-2506.*
(Continued)

*Primary Examiner* — Nathan R Price
*Assistant Examiner* — Melissa A Snyder
(74) *Attorney, Agent, or Firm* — Marshall, Gerstein & Borun LLP (57) ABSTRACT

A drug delivery device (100) includes a base (102) having a first region (104) with a drug delivery assembly (106) associated therewith. The drug delivery device also includes an antenna (112) disposed in the first region to radiate an electromagnetic field, the base defining a plane (114) and the antenna disposed in the plane of the base, and an electro-
(Continued)

magnetic field generator (116) selectively coupled to the antenna.

24 Claims, 4 Drawing Sheets

(52) U.S. Cl.
CPC ............... *A61M 2037/0023* (2013.01); *A61M 2037/0046* (2013.01); *A61M 2037/0061* (2013.01); *A61N 1/0412* (2013.01); *A61N 1/0428* (2013.01); *A61N 1/325* (2013.01)

(56) References Cited

U.S. PATENT DOCUMENTS

| | | | |
|---|---|---|---|
| 6,656,147 B1 | 12/2003 | Gertsek et al. | |
| 6,689,100 B2 | 2/2004 | Connelly et al. | |
| 6,689,380 B1 | 2/2004 | Marchitto et al. | |
| 6,808,506 B2 | 10/2004 | Lastovich et al. | |
| 7,066,922 B2 | 6/2006 | Angel et al. | |
| 7,156,838 B2 | 1/2007 | Gabel et al. | |
| 7,214,221 B2 | 5/2007 | Fentress et al. | |
| 7,250,037 B2 | 7/2007 | Shermer et al. | |
| 7,252,651 B2 | 8/2007 | Haider et al. | |
| 7,410,476 B2 | 8/2008 | Wilkinson et al. | |
| 7,556,615 B2 | 7/2009 | Pettis et al. | |
| 7,645,263 B2 | 1/2010 | Angel et al. | |
| 7,645,264 B2 | 1/2010 | Marsh et al. | |
| 7,651,475 B2 | 1/2010 | Angel et al. | |
| 7,654,983 B2 | 2/2010 | De La Serna et al. | |
| 7,967,772 B2 | 6/2011 | McKenzie et al. | |
| 8,062,783 B2 * | 11/2011 | Carter | A61N 1/044 429/122 |
| 8,105,283 B2 | 1/2012 | Perriere | |
| 8,540,672 B2 | 9/2013 | McAllister | |
| 8,834,454 B2 | 9/2014 | Genosar et al. | |
| 9,011,376 B2 | 4/2015 | Genosar et al. | |
| 2003/0014014 A1 | 1/2003 | Nitzan | |
| 2003/0045837 A1 * | 3/2003 | Delmore | A61M 37/0015 604/173 |
| 2003/0060780 A1 | 3/2003 | Shu | |
| 2003/0083618 A1 | 5/2003 | Angel et al. | |
| 2003/0083619 A1 | 5/2003 | Angel et al. | |
| 2003/0083645 A1 | 5/2003 | Angel et al. | |
| 2003/0181863 A1 | 9/2003 | Ackley et al. | |
| 2004/0143213 A1 | 7/2004 | Hunter et al. | |
| 2004/0162518 A1 | 8/2004 | Connelly et al. | |
| 2005/0010193 A1 | 1/2005 | Laurent et al. | |
| 2005/0065472 A1 | 3/2005 | Cindrich et al. | |
| 2005/0085766 A1 | 4/2005 | Trautman et al. | |
| 2005/0165358 A1 * | 7/2005 | Yeshurun | A61M 37/0015 604/173 |
| 2005/0277887 A1 | 12/2005 | Douglas et al. | |
| 2007/0038181 A1 | 2/2007 | Melamud et al. | |
| 2007/0276318 A1 * | 11/2007 | Henley | A61B 17/205 604/20 |
| 2008/0114298 A1 | 5/2008 | Cantor et al. | |
| 2008/0281273 A1 | 11/2008 | Angel et al. | |
| 2009/0012494 A1 | 1/2009 | Yeshurun et al. | |
| 2009/0099522 A1 | 4/2009 | Kamen et al. | |
| 2009/0137945 A1 | 5/2009 | Marquez | |
| 2009/0163868 A1 | 6/2009 | Hoel et al. | |
| 2009/0209911 A1 | 8/2009 | Cabus et al. | |
| 2009/0247953 A1 | 10/2009 | Yeshurun et al. | |
| 2010/0030152 A1 | 2/2010 | Lee et al. | |
| 2010/0256465 A1 | 10/2010 | Bernstein et al. | |
| 2011/0117150 A1 | 5/2011 | Eckhoff et al. | |
| 2011/0172609 A1 | 7/2011 | Moga et al. | |
| 2011/0172637 A1 | 7/2011 | Moga et al. | |
| 2011/0172638 A1 | 7/2011 | Moga et al. | |
| 2011/0172639 A1 | 7/2011 | Moga et al. | |
| 2011/0172645 A1 | 7/2011 | Moga et al. | |
| 2011/0306853 A1 * | 12/2011 | Black | A61B 5/1468 600/309 |
| 2012/0083748 A1 | 4/2012 | Harms et al. | |
| 2012/0109066 A1 | 5/2012 | Chase et al. | |
| 2012/0123387 A1 | 5/2012 | Gonzalez et al. | |
| 2012/0238938 A1 | 9/2012 | Herekar et al. | |
| 2012/0310169 A1 | 12/2012 | Sonderegger et al. | |
| 2012/0310173 A1 | 12/2012 | Sonderegger | |
| 2012/0310175 A1 | 12/2012 | Vedrine et al. | |
| 2012/0323183 A1 | 12/2012 | Peterson et al. | |
| 2013/0006195 A1 | 1/2013 | Sonderegger et al. | |
| 2013/0006196 A1 | 1/2013 | Sonderegger et al. | |
| 2013/0030841 A1 | 1/2013 | Bergstrom et al. | |
| 2013/0102954 A1 | 4/2013 | Choi | |
| 2013/0110043 A1 | 5/2013 | Levin | |
| 2013/0226098 A1 | 8/2013 | Tokumoto et al. | |
| 2013/0338589 A1 | 12/2013 | Cindrich et al. | |
| 2013/0345638 A1 | 12/2013 | Heidenreich et al. | |
| 2014/0005606 A1 | 1/2014 | Chen et al. | |
| 2014/0094756 A1 | 4/2014 | Bobroff et al. | |
| 2014/0243786 A1 | 8/2014 | Gilbert et al. | |
| 2014/0249355 A1 * | 9/2014 | Martinez | A61N 2/02 600/14 |
| 2014/0296782 A1 | 10/2014 | Ulrich et al. | |
| 2014/0296825 A1 | 10/2014 | Lemaire et al. | |
| 2015/0080844 A1 | 3/2015 | Donovan et al. | |
| 2015/0141954 A1 | 5/2015 | Da Ros et al. | |
| 2015/0157809 A1 | 6/2015 | Park et al. | |

OTHER PUBLICATIONS

Sullivan, et al. Effect of a Monoclonal Antibody to PCSK9 on Low-Density Lipoprotein Cholesterol Levels in Statin-Intolerant Patients. Dec. 19, 2012. Journal of the American Medical Association. vol. 308, No. 23. 2497-2506. (Year: 2012).*
International Preliminary Report on Patentability and Written Opinion of the International Searching Authority, dated Aug. 9, 2016.
International Search Report for PCT/US2015/014162, dated Apr. 23, 2015.

* cited by examiner

DRUG DELIVERY SYSTEM WITH ELECTROMAGNETIC FIELD GENERATOR

CROSS-REFERENCE TO RELATED APPLICATIONS

The present application is the United States National Phase of International Patent Application No. PCT/US2015/014162, filed Feb. 3, 2015, which claims priority to U.S. Provisional Patent Application No. 61/936,125, filed Feb. 5, 2014, the entirety of each of the foregoing priority applications is hereby incorporated herein by reference.

FIELD OF THE DISCLOSURE

This present disclosure is directed to a drug delivery system and, more particularly, a transdermal drug delivery system.

BACKGROUND

Drug delivery can be accomplished through any one or more of a variety of conventional means. For example, many drugs are consumed orally through capsules or pills. Another common technique for drug delivery is through the use of a needle or cannula, such as those used with standard syringes, catheters, auto-injectors, on-body injectors, etc. Needles and catheters are generally introduced through the patient's skin to access the desired delivery site for the particular medication being administered. Still other means for achieving drug delivery include transdermal patches. A transdermal patch is a medicated adhesive patch that is placed on the patient's skin to deliver a specific dose of medication through the skin and into the bloodstream. Some advanced versions of such patches can even include arrays of microneedles that very slightly penetrate the patient's skin and/or create a wound to increase skin permeability and facilitate drug delivery.

SUMMARY

According to an aspect of the present disclosure, a drug delivery device includes a base having a first region with a drug delivery assembly associated therewith. The drug delivery device also includes an antenna disposed in the first region to radiate an electromagnetic field, the base defining a plane and the antenna disposed in the plane of the base, and an electromagnetic field generator selectively coupled to the antenna.

According to another aspect of the present disclosure, a method of delivering a drug to a patient includes applying a drug delivery device to the patient, the delivery device including a base having a first region with a drug delivery assembly associated therewith, and an antenna disposed in the first region to radiate an electromagnetic field, the base defining a plane and the antenna disposed in the plane of the base. The method also includes generating an electromagnetic field using the antenna, the electromagnetic field causing migration of cells within the patient relative to the delivery device, and delivering a drug to the patient via the drug delivery assembly.

According to a further aspect of the present disclosure, a drug delivery device includes a base having a first region with a plurality of microneedles disposed thereon and a second region with adhesive disposed thereon. The microneedles have a conical wall with a first end attached to the base and a second end with an opening, and an inner surface and an outer surface, the inner surface defining a needle reservoir in communication with the opening. The device also includes an antenna disposed in the first region within the plurality of microneedles to radiate an electromagnetic field, the base defining a plane and the antenna disposed in the plane of the base, and an electromagnetic field generator selectively coupled to the antenna.

BRIEF DESCRIPTION OF THE DRAWINGS

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DESCRIPTION OF VARIOUS EMBODIMENTS

The specification provides a description of a drug delivery device that can be used with biologics or other medicaments. For example, biologics may be proteins, monoclonal antibodies, or even a solution containing a biological agent in solution, e.g., a solution containing a virus.

Various embodiments of the invention can provide advantages over subcutaneous injection for treating diseases. The advantages can include, but are not limited to one or more of the following: higher treatment efficiencies, fewer side effects, decreased pain levels, decreased infection rates or localized/targeted delivery of a drug.

Figure 1:
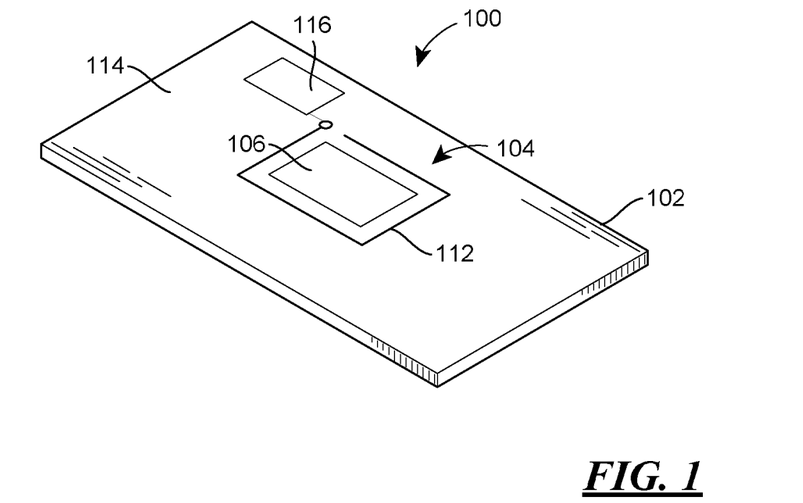
FIG. 1 is a perspective view of an embodiment of a general form of the drug delivery device according to the present disclosure.

FIG. 1 illustrates a general form of a drug delivery device 100 according to the present disclosure. The drug delivery device 100 includes a base 102, the base 102 having a first region 104 with drug delivery assembly 106 disposed thereon. The drug delivery assembly 106 may include such structures as cannulas, needles, microneedles, jet injectors, etc. and associated reservoirs, drives, etc. that may be used to deliver a drug to the patient, preferably but not exclusively transdermally. The details of such an assembly 106 are discussed in greater detail below, and with reference to various specific embodiments. Examples of microneedle devices have been described in U.S. Pat. Nos. 6,334,856 and 7,226,439, which patents are incorporated herein by reference in their entirety.

The drug delivery device 100 also includes an antenna 112 disposed in the first region 104 to radiate an electromagnetic (EM) field. The base 102 defines a plane 114, and the antenna 112 is disposed in the plane 114 of the base 102. An EM field generator 116 is selectively coupled to the antenna 112 to generate the EM field. In some embodiments, the EM may be pulsed.

Figure 2:
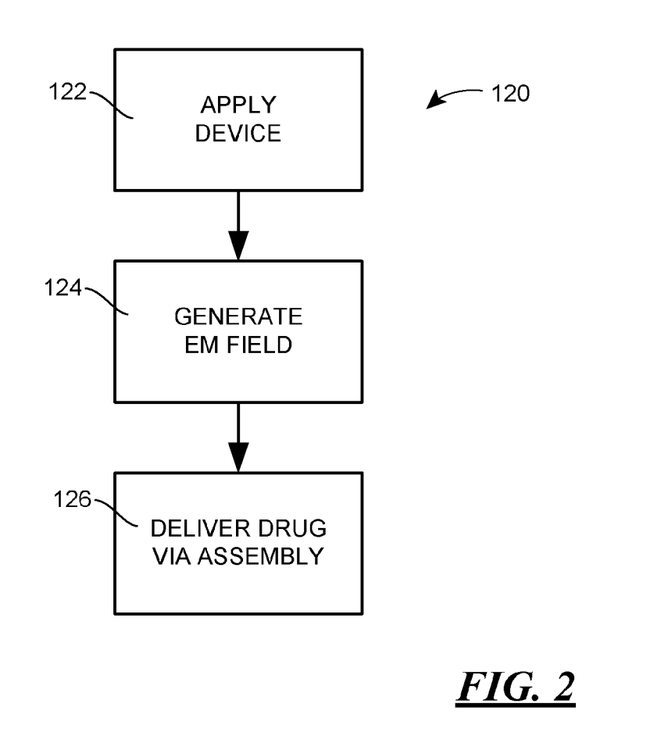
FIG. 2 is an embodiment of a method of operating the drug delivery device of FIG. 1.

According to such an embodiment, a method 120 of delivering a drug to a patient may be described and is illustrated in FIG. 2. In particular, such the method 120 may include applying the drug delivery device 100 to the patient at block 122. In particular, the base 102 may be applied to the skin of the patient, although the method 120 may encompass application to the patient that does not include an on-body attachment or adhesive (i.e., the drug delivery device 100 is held in place when applied to the patient, for example, by hand). The method 120 may further include generating an EM field using the antenna 112, the EM field causing migration of cells within the patient relative to the delivery device 100, at block 124. Further, the method 120 may include delivering a drug to the patient via the drug delivery assembly 106 at block 126. The application of a pulsed EM field is expected to enhance microcirculation and blood vessel permeability in the patient, thus facilitating drug transfer to the systemic circulation. In addition, delivering a pulsed EM field prior to and/or during topical application of a drug may facilitate skin penetration, increase kinetic energy, increase drug uptake and absorption. The device 100 may be left in place for hours or days for long-term administration of a drug to patient, or the period of application may be much shorter, on the order of minutes to one or two hours.

The pulsed EM field generated using the antenna 112 is applied to the skin or other tissues, rather than to the drug to be delivered by the drug delivery assembly 106, although in some embodiments a separate EM field may be applied to the drug to be delivered by the drug delivery assembly 106. Without being limited to a specific mechanism of action the EM field radiated by the antenna 112 causes the migration of cells within the patient relative to the delivery device 100. Additionally, the amount of drug required to be delivered to the patient may be reduced relative to conventional methods because the drug delivery can be localized or targeted. The migration of the cells and increased local blood circulation may be reversible once the EM field is no longer generated. With a pulsed EM field, the kinetic energy may (i) cause drug absorption to the deeper tissue, into the dermis and beyond (even though the field does not cause the drug to exit the delivery device 100) and (ii) open interstitial spaces to permit the drug to move more freely within the tissue to the targeted cells.

Figure 3:
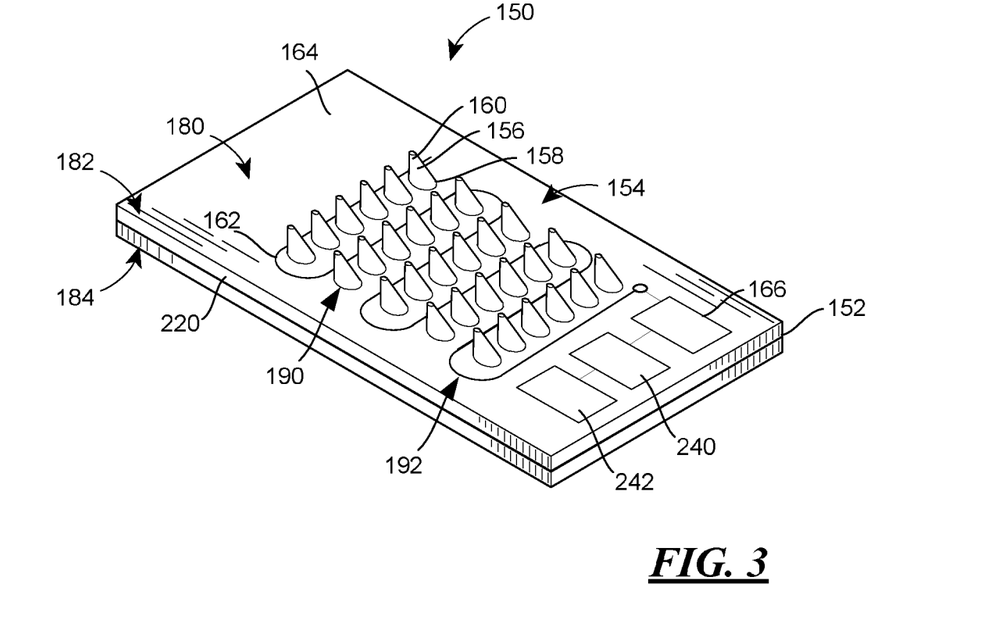
FIG. 3 is a perspective view of an embodiment of a drug delivery device according to the present disclosure including microneedles.

A particular embodiment of the drug delivery device 150 is shown in FIG. 3. The drug delivery device 150 includes a base 152, the base 152 having a first region 154 with a plurality of microneedles 156 disposed thereon. The microneedles 156 each have a first end 158 attached to the base 152 and a second end 160 depending from (e.g., spaced from) the base 152. The details of the microneedles 156 is discussed in greater detail below, but it will be noted that the attachment of the microneedles 156 may come about as a consequence of the fabrication of the microneedles 156 on the base 152, such that the attachment between the microneedles 156 and the base 152 may be characterized as integral (i.e., one piece).

The drug delivery device 150 also includes an antenna 162 disposed in the first region 154 and positioned between at least some of the plurality of microneedles 156 to radiate an EM field. The base 152 defines a plane 164 in which the first ends 158 of the micro-needles reside, and the antenna 162 is disposed in the plane 164. An EM field generator 166 is selectively coupled to the antenna 162 to generate the EM field.

Figure 4:
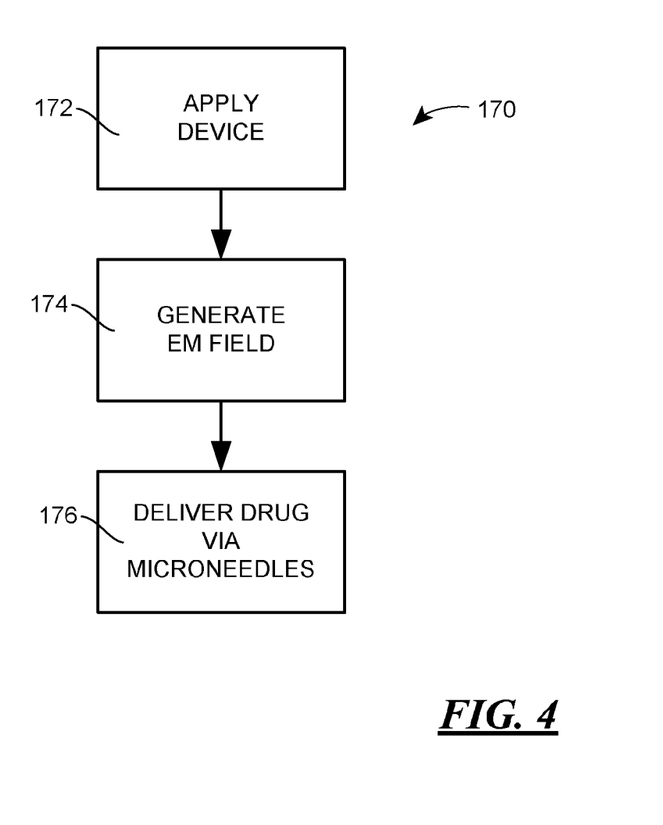
FIG. 4 is an embodiment of a method of operating the drug delivery device of FIG. 3.

According to such an embodiment, a method 170 of delivering a drug to a patient may be described in reference to FIG. 4. In particular, the method 170 may include applying the drug delivery device 150 to the patient at block 172. In particular, the base 102 may be applied to the skin of the patient. The method 170 may further include generating an EM field using the antenna 162 at block 174, the EM field presumably causing migration of cells within the patient relative to the delivery device 150. Further, the method 170 may include delivering a drug to the patient via the microneedles 156 at block 176.

Having described a general form and operation of the drug delivery device 100 and a particularized form and operation of the drug delivery device 150, the details of each may be described in further detail.

According to the embodiment of FIG. 1, the drug delivery assembly 106 may include a variety of features, with multiple subassemblies. For example, the drug delivery assembly 106 may include a cannula, needle, microneedle or other fluid delivery device to deliver a material or drug to a patient. The material or drug may be contained in a reservoir or other storage device, which reservoir or storage device is or may be placed in fluid communication with the cannula, needle, microneedle or other fluid transport device. The reservoir may be associated with a drive to cause the material in the reservoir to flow from the reservoir through the cannula, needle, microneedle, etc. to the patient. For example, the drive may include a spring that moves a wall of the reservoir (defined by a plunger, for example) relative to an opening to eject material from the reservoir. The drive might also include a motor or other mechanical device that operates to move a wall of the reservoir. The drive may instead include a chemical subassembly that moves a wall of the reservoir based on the production of a gas that acts against the wall. As a further alternative, the drive may generate an electrical field that causes the material to leave the reservoir and enter the patient. In fact, according to such an embodiment, it may not be necessary to provide a cannula, needle, microneedle or other fluid transport device.

As a non-exhaustive list, the drug delivery assembly 106 may deliver a material or drug using needle injection, jet injection, and/or iontophoresis. A specific drug delivery assembly is provided in the embodiment of FIG. 3, wherein the assembly includes a plurality of microneedles 156.

The base 152 may be made from a variety of materials or combinations of materials. For example, the base 152 may be made of polymers, copolymers, and combinations, blends or composites thereof. Considering that an antenna 162 is intended to be attached to or embedded in the base 152, the material of the base 152 may be selected with this consideration in mind as well. For example, the base 152 may include metals, ceramics, or semiconductor materials to facilitate the joining of the antenna 162 to the base 152.

While the base 152 may have some degree of flexibility to conform to the shape of the patient, the material for the base 152 may also be selected to have a degree of rigidity to allow the microneedles 156 to be applied with sufficient force to pass through the outer layer of the skin. To this end, the base 152 may be a composite of more than one material, so as to provide a suitably rigid structure to ensure needle placement and a suitably flexible structure to accommodate irregularities in the application site. Flexibility may also facilitate more consistent penetration of the outer layer(s) of the skin by the microneedles 156, because penetration can be affected by irregularities in the skin surface.

Further, it will be recognized that the base 152 has a second region 180, the first region 154 and the second region 180 being on a common, first side 182 of the base 152. In fact, the base 152 may have a second side 184 opposite that of the first side 182 of the base 152. With the device 150 oriented as illustrated in FIG. 3, the first side 182 may be referred to as the proximal side or the proximal surface, and the second side 184 may be referred to as the distal side or the distal surface. Such reference is relative to the patient with respect to the orientation of the drug delivery device 150 when applied to the patient, and is for ease of illustration and not by way of limitation.

While the first region 154 may have a plurality of microneedles 156 attached thereto, the second region 180 may have an adhesive disposed thereon. The adhesive may be of a type that readily adheres to skin, and which may be removed from the skin once the drug delivery device 150 has been used. For example, a pharmaceutical grade adhesive may be used. Prior to use, a cover, shield or other layer may be disposed over the first and second regions 154, 180, the cover, shield or other layer being removed immediately prior to application to the patient's skin.

The second region 180 may adjoin the first region 154 in addition to being on the same side 182 of the base 152. In particular, the second region 180 may adjoin the first region 154 such that there is no intervening area or space between the first region 154 and the second region 180 (i.e., the second region 180 may directly adjoin the first region 154). In addition, the second region 180 may be disposed about the first region 154. That is the second region 180 may be defined by a section or sections of the proximal surface 182 continuously or discontinuously arranged such that the first region 154 does not depend further outward from the center of the first region 154 than the outermost portions of the second region 180. According to one embodiment of the present disclosure, the second region 180 may completely surround the first region 154 in that the second region 180 is defined continuously about the first region 154 such that no portion of the first region 154 exists spatially outside the second region 180.

The converse also may be true: the first region 154 may be disposed adjoining the second region 180. In fact, the first region 154 may disposed about the second region 180, and may even surround the second region 180. It is also possible for the regions 154, 180 to be intermixed.

Rather than using an adhesive applied to a region 180 of the base 152, the adhesive may be disposed on a holder to which the base 152 is attached. As a further alternative, a band or strip of material may be disposed about the patient (e.g., the patient's arm, leg or torso) with the drug delivery device 150 disposed between the band or strip and the patient, which strip or band may not have an adhesive disposed thereon. In such a fashion, the drug delivery device 150 may be applied and held in place without the use of adhesive. It will also be recognized that the drug delivery device 150 could be held in place by hand, or potentially even through the interaction of the microneedles 156 and the skin. For example, the microneedles 156 may embed themselves into the skin, and biodegrade to a point at which the base 152 is no longer attached to the microneedles, at which point the base 152 may fall away from the patient.

As noted above, the microneedles 156 are attached at a first (bottom) end 158 to the base 152 and have a second (top) end 160 that depends from (e.g., spaced from) the base 152. More particularly, the first end 158 of the microneedles 156 is attached to the proximal side 182 of the base 152. The second end 160 may be described as cantilevered from the base 152, the first end 158, and/or the first or proximal side 182 in that the second end 160 depends in an unsupported fashion from the base 152, the first end 158, or the proximal side 182.

Figure 5:
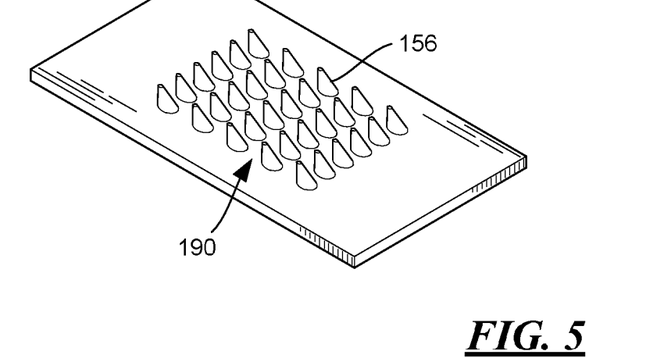
FIG. 5 is a perspective view of an embodiment of the drug delivery device of FIG. 3 illustrating a first exemplary array.
Figure 6:
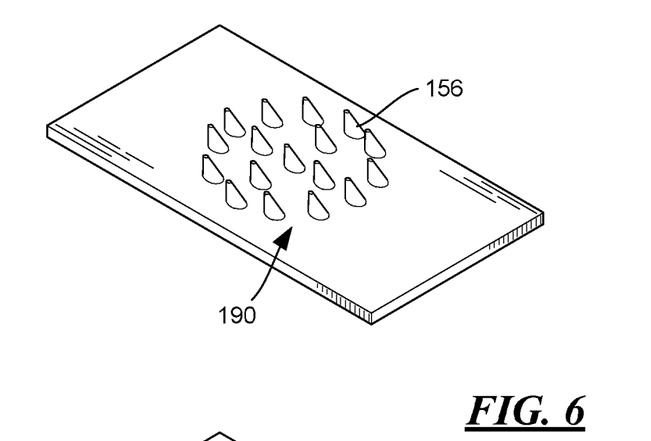
FIG. 6 is a perspective view of an embodiment of the drug delivery device of FIG. 3 illustrating a second exemplary array.
Figure 7:
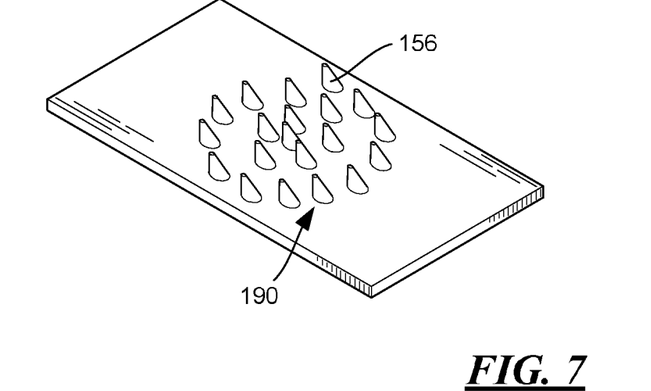
FIG. 7 is a perspective view of an embodiment of the drug delivery device of FIG. 3 illustrating a third exemplary array.

According to certain embodiments, the microneedles 156 may be disposed on the first region 154 of the base 152 without regard for a regular pattern. However, the microneedles 156 may be disposed on the proximal side 182 of the base 152 within the first region 154 so as to define an array 190 (i.e., a systematic or ordered arrangement) of microneedles 156. For example, the array 190 may be defined by a grid pattern, wherein the microneedles 156 are arranged in a number of rows and columns. See, e.g., FIG. 5. Alternatively, the array 190 may be defined by disposing the microneedles 156 on the base 152 in a series of concentric circles or other geometric objects (e.g., polygons). See, e.g., FIG. 6. As a still further embodiment of the present disclosure, the array 190 may be defined by disposing the microneedles 156 in a spiral within the first region 154. See, e.g., FIG. 7.

It will be recognized that the microneedles 156 within the region 154 may define more than one array 190. In fact, the region 154 may include microneedles 156 defining one or more arrays 190 as well as microneedles 156 arranged without regard for an ordered or regular arrangement. Further, the arrays 190 themselves may be defined according to different principles of arrangement: one array 190 may have the microneedles 156 arranged in rows and columns while another array 190 may be defined by a series of concentric polygons. All combinations for the arrangement of the microneedles 156 within the region 154 are encompassed within the present disclosure.

The dose administered to the patient will be influenced by the density of the microneedles 156, as well as the size of the first region 154. For example, to increase the dose, the density of the microneedles 156 may be increased. Alternatively, the size of the first region 154 may be increased, such that a larger number of microneedles are included for a single drug delivery device 150 to deliver a larger dose. As a further alternative, the size of the individual microneedle 156 may be varied to vary the dose delivered.

The antenna 162 may be disposed in a pattern within the first region 154. In particular, the antenna 162 may be disposed in the array 190 of microneedles 156. For example, the antenna 162 may be disposed in a serpentine pattern 192 within the array 190 of microneedles 156 as illustrated in FIG. 3. In such an embodiment, the antenna 162 passes between adjoining instances of the microneedles 156, such that the microneedles 156 may be described as being disposed on opposite sides of the antenna 162. In FIG. 3, the antenna 162 can be described as passing between adjacent rows or columns of microneedles 156.

Figure 8:
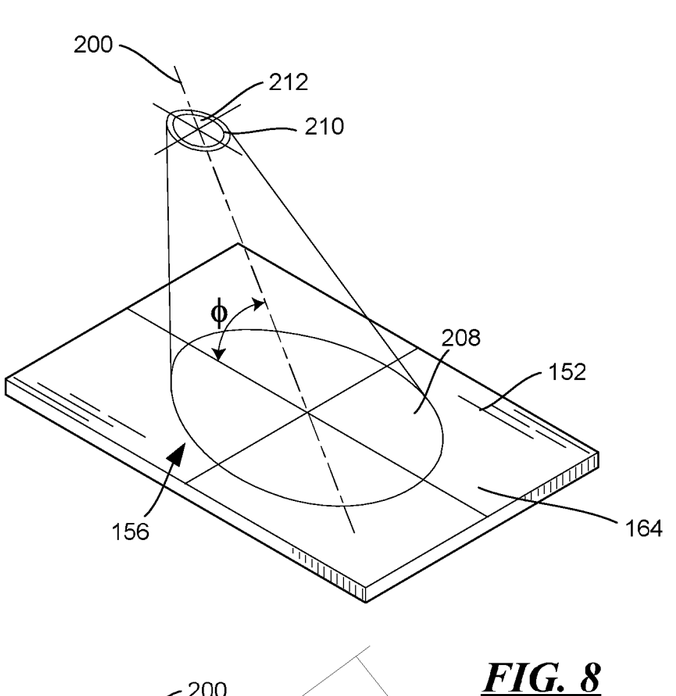
FIG. 8 is an enlarged perspective view of an embodiment of a microneedle for use in the drug delivery device of FIG. 3.

Each microneedle 156 may have a longitudinal axis 200 that depends (e.g., extends) between the first and second ends 158, 160 of the microneedles 156. See FIGS. 8 and 9. This axis 200 may be disposed at an angle φ relative to the plane 164 of the base 152 when the base 152 occupies a planar configuration, as shown in FIG. 8, for example.

Similar to the arrangement of the microneedles 156 into one or more arrays 190 discussed above, the microneedles 156 attached to a first section of the first region 154 may not be disposed at the same angle φ to the plane 164 as microneedles 156 attached to a second section of the first region 154. While microneedles 156 arranged at right angles (i.e., orthogonal) to the plane 164 of the base 152 may permit a greater density of microneedles 156 per unit area, it is believed that microneedles 156 arranged at an angle φ less than 90 degrees to the plane 164 of the base 152 may facilitate the penetration of the microneedles 156 into the skin, potentially reducing the insertion force and improving patient tolerability.

According to certain embodiments, the angle φ of the axis 200 is between approximately 15 degrees and approximately 90 degrees relative to the plane 164 of the base 152 (i.e., the angle φ may be approximately 15-degrees, approximately 90-degrees, or any angle between these endpoints). According to other embodiments, the axis 200 may be disposed at an angle φ of between approximately 15 degrees and approximately 45 degrees or at an angle φ of between approximately 20 degrees and approximately 40 degrees relative to the plane 164 of the base 152. The axis 200 may be disposed at and angle φ within any of the ranges described above (between approximately 15 degrees and approximately 90 degrees, between approximately 15 degrees and approximately 45 degrees, or between approximately 20 degrees and approximately 40 degrees) for substantially all of the plurality of microneedles 156. According to the method used to attach the microneedles 156 to the base 152, it may be practically impossible to ensure that each and every one of the microneedles 156 is arranged at a particular angle φ relative to the base. Consequently, to the extent that the axis 200 is described as disposed at an particular angle φ (or range of angles) for substantially all of the plurality of microneedles 156, this statement embraces an embodiment wherein a large percentage (e.g., 80%, 90%, 95%, 98% or 99%) of the microneedles 156 are actually disposed within a range including the particular angle φ, which range may or may not be centered about the particular angle φ.

According to one embodiment, the axis 200 is disposed at approximately 30 degrees to the plane 164 of the base 152 at least for a majority of the plurality of microneedles 156, which orientation may facilitate targeting of the skin pores and may prevent plugging that may otherwise occur at the needle/skin interface. In fact, according to a further embodiment, the axis 200 is disposed at approximately 30-degrees for substantially all of the plurality of microneedles 156. As mentioned above, according to the method used to attach the microneedles 156 to the base 152, it may be practically impossible to ensure that each and every one of the microneedles 156 is arranged at the particular angle φ relative to the base. Consequently, to the extent that the axis 200 is described as disposed at approximately 30-degrees for substantially all of the plurality of microneedles 156, this statement embraces an embodiment wherein a large percentage (e.g., 80%, 90%, 95%, 98% or 99%) of the microneedles 156 are actually disposed within a range including 30 degrees (e.g., approximately 25 degrees to approximately 35 degrees, approximately 28 degrees to approximately 32 degrees, or approximately 29 degrees to approximately 31 degrees), which range may or may not be centered about approximately 30 degrees (e.g., the range may encompass approximately 29 degrees to approximately 32 degrees or approximately 28 degrees to approximately 31 degrees).

Figure 9:
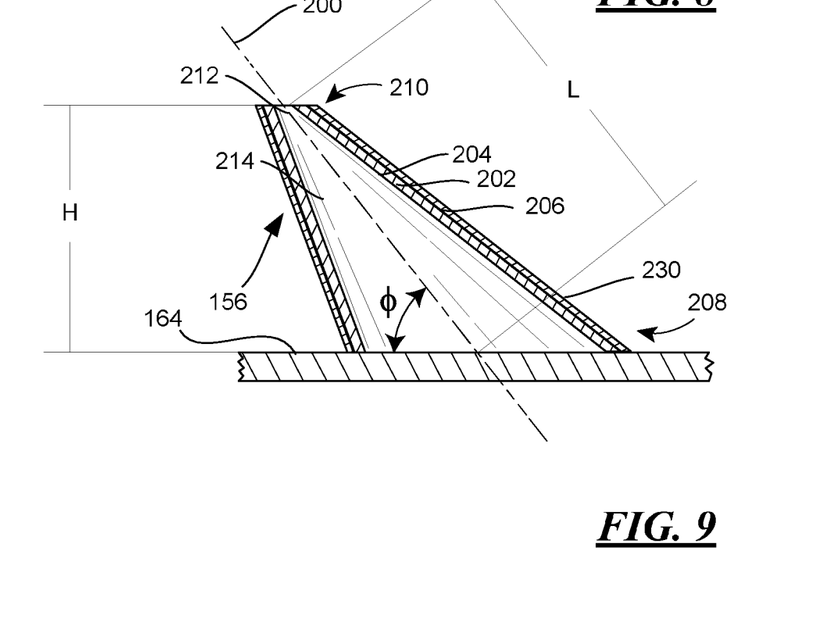
FIG. 9 is a cross-sectional view of the microneedle of FIG. 8.

According to the embodiment illustrated in FIGS. 8 and 9, each of the microneedles 156 may have a wall 202 having an inner surface 204 and an outer surface 206. The wall 202 may depend (e.g., extend) from a first end 208 to a second end 210, the first end 208 also being referred to as a proximate end and the second end 210 also being referred to as a distal end, proximate and distal being referenced with respect to the surface 182. The wall 202 may terminate in an aperture or opening 212 at the second end 210 of the wall 202. The aperture or opening 212 may be formed prior to insertion of the microneedle 156 into the skin, or the aperture or opening 212 may be formed as a consequence of the insertion of the microneedle 156 into the skin.

The microneedles 156 may be described as having a height H (see, FIG. 9), which may be defined as a distance between the plane 164 of the base 152 and the second end 210 along a line orthogonal to the plane 164 of the base 152. The microneedles 156 may also be described as having a length L (see, FIG. 9), which may be defined as a distance between the first end 208 and the second end 210 along the central axis 200. Where the microneedle 156 is attached to the base 152 such that the axis 200 is orthogonal to the plane 164 of the base 152, the height H and the length L may be the same. However, where the axis 200 of the microneedle 156 is at the angle φ to the place 164 of the base 152, the height H of the microneedles 156 may be less than the length L of the microneedles. According to certain embodiments, the microneedles 156 have a height H of between approximately 400 and approximately 1000 microns to permit a transdermal administration of the material to be delivered (e.g., to enter the epidermis). Other embodiments may include microneedles 156 having a height H of between approximately 400 and approximately 800 microns or between approximately 800 and approximately 1000 microns, for example. Of course, this does not prevent different needle sizes in other embodiments.

The wall 202 may be continuous, such that the inner and outer surfaces 204, 206 are continuous in a cross-sectional plane, for example a cross-sectional plane that is parallel to the plane 164. As such, with the wall 202 attached to the base 152 at the first end 208, material disposed within the microneedle 156 may exit only through the aperture 212 according to an embodiment wherein the wall 202 is not biodegradable. Alternatively, the wall may be discontinuous, such that the inner and outer surfaces are discontinuous in the cross-sectional plane, defining side openings, channels, pores or slots between the first and second ends 208, 210. As a further alternative, the wall 202 may be biodegradable, such that portions of the wall 202 may disappear over time, either increasing the size of the aperture 212 and/or forming side openings or slots. All such possibilities are within the scope of the present disclosure.

As to the cross-section of the wall 202, the cross-section 202 may be hollow, such that the inner surface 204 defines a needle reservoir 214 in communication with the opening 212. According to the illustrated embodiment, the wall 202 may be generally truncated and conical in shape, with its central axis 200 disposed at the angle φ such that the cross-section in a plane parallel to the plane 164 forms a tear-drop shape. Alternatively, the wall 202 may have straight walls instead (e.g., such as in a cylinder) or the tapered wall 202 forming a conical shape, the central axis 200 of which may not be disposed at the angle φ to the plane 164 of the base 152. In fact, the wall 202 may have different shapes in cross-section along the length L of the microneedle 156. The greatest dimension across a given cross-section taken with respect to the outer surface 206 of the microneedle 156 may be between approximately 1 micron and approximately 500 microns, although this may more typically be in the range of approximately 10 microns and approximately 100 microns, or even approximately 30 microns to approximately 40 microns. A dimension of approximately 30 microns to approximately 40 microns would be suitable for use with skin, wherein the average skin pore size is approximately 50 microns. The greatest dimension at the second end 210 may be considerably less than approximately 30 microns to 40 microns; for example, the greatest dimension at the second end 210 may be approximately 15 microns. Further, while the greatest dimension across a given cross-section taken with respect to the outer surface 206 may be approximately 30 microns to approximately 40 microns, the greatest dimension across the same cross-section with respect to the inner surface 204 may be substantially less.

The second end 210 of the wall 202 of the microneedle 156 may have a different profile than the remainder of the wall 202. For example, according to certain embodiments, the second end 210 of the microneedle is beveled like a conventional needle. Other configurations are possible. For example, the second end 210 may be tapered. The second end 210 may be symmetrical or asymmetrical.

A material to be delivered by the microneedles 156, for example a therapeutic, may be disposed in the needle reservoir 214. In fact, the needle reservoir 214 may include one or more chamber, which in the case of a plurality (i.e., more than one) of chambers may be defined by disposing one or more walls within the needle reservoir 214. In those embodiments wherein a plurality of chambers is provided, each chamber may have a different material disposed therein, such that multiple materials may be administered to the patient concurrently. Alternatively, the materials in separate chambers may be separated by a degradable wall that permits the materials in separate chambers to mix within the reservoir 214 prior to administration to the patient, for example. As a further alternative, different microneedles 156 within an array 190 of microneedles 156 may have different materials disposed in their respective needle reservoirs 214 to permit concurrent administration to the patient.

According to certain embodiments, the base 152 includes a drug diffusion layer 220 (see, FIG. 3) in communication with the needle reservoir 214. According to such embodiments, a material to be delivered by the microneedles 156 may be disposed within the drug diffusion layer 220, which material then is transferred between the drug diffusion layer 220 and the needle reservoir 214, and then is delivered to the patient from the needle reservoir 214. In the alternative, the drug diffusion layer 220 may be replaced with a reservoir that is attached, for example, to the proximal or the distal side 182, 184 of the base 152 using an adhesive, for example.

According to alternative embodiments, the material to be delivered may be disposed within the wall 202, such as in pores, pockets, notches or grooves formed in the outer surface 206 of the wall 202. In fact, the wall 202 may be molded of a material that is a mixture of the material to be delivered dispersed in a polymer liquid or polymer solution. As a further alternative, the polymer may be biodegradable, such that the wall 202 degrades over time to expose pores or pockets of the material to be delivered to the patient. These pores, pockets, notches or grooves may be interconnected to permit material to transfer from pore to pore, or may be discrete such that the material in the pore, pocket, notch or groove is only released when the biodegradable material degrades.

As mentioned above, the microneedles 156 may be biodegradable or non-biodegradable, in whole or in part. That is, the microneedles may be in part biodegradable and in part non-biodegradable. An exemplary biodegradable material is polyethylene.

In general terms, the microneedles 156 may be made of metals, ceramics, semiconductor materials, polymers and composites. Where a polymer is used, the polymer may be selected from biocompatible, biodegradable polymers such as poly(lactide)s, poly(glycolide)s, poly(lactide-co-glycolide)s, polyanhydrides, polyorthoesters, polyetheresters, polycaprolactones, polyesteramides, poly(butyric acid), poly(valeric acid), polyurethanes and copolymers and blends thereof. Alternatively, non-biodegradable polymers may include polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

The microneedles 156 may be formed using a variety of processes. For example, arrays 190 of microneedles 156 can be fabricated, for example, using combinations of dry etching processes; micromold creation in lithographically-defined polymers and selective sidewall electroplating; or direct micromolding techniques using epoxy mold transfers. For example, microneedles can be fabricated by (i) etching the polymer microneedle directly, (ii) etching a mold and then filling the mold to form the polymer microneedle product, or (iii) etching a microneedle master, using the master to make a mold, and then filling the mold to form the polymer microneedle replica (of the master). Alternatively, rather than using etching processes (e.g., RIE, photolithography) to define the microneedle or mold shape, special physical cutting tools with very sharp tips/cutting edges can be used. Where micromolding is used, microfabrication techniques such as photolithography, plasma etching, or laser ablation can first be used to make a mold form, the mold form is then transferred to other materials using standard mold transfer techniques, such as embossing or injection molding, and followed by reproduction of the shape of the original mold form using the newly-created mold to yield the final microneedles. Alternatively, the step of fabrication of the mold form could be eliminated and the mold could be microfabricated directly, which could then be used to create the final microneedles. Exemplary processes and structures are described in U.S. Pat. Nos. 6,503,231 and 6,334,856, U.S. Publ. No. 2002/0082543 and PCT Publ. Nos. WO 99/64580 and WO 00/74763, which patents and publications are incorporated herein by reference in their entirety.

In addition, according to certain embodiments, a layer 230 of antimicrobial agent disposed on the outer surface 206 of the microneedles 156 to inhibit bacterial growth. The layer 230 may be continuously disposed on the surface 206 between the first and second ends 208, 210, or the layer 230 may be discontinuous (e.g., in bands or strips alternating with regions without the antimicrobial agent present).

The administration of the material from the microneedles 156 may occur without any drive being used to cause the material to exit the microneedles 156. However, the microneedles 156 may be used in connection with a mechanism that encourages the material to leave the reservoir 214 and enter the patient. For example, such a mechanism may use pressure gradients, concentration gradients, electricity, ultrasound, receptor binding, heat, chemicals, and/or chemical reactions. Mechanical valves also may be used in conjunction with the mechanisms described above to selectively control transport of the material.

The administration of the material from the microneedles 156 may be related to the material used to form the microneedles. For example, the microneedles 156 may be made of a polymer that is sensitive to EM radiation, and specifically is sensitive to EM radiation to control such attributes as elution. As a consequence, an EM field applied to the microneedles 156 may control the delivery rate, as well as have the effects mentioned above and below relative to cellular response. As one, non-limiting example, such materials may include magnetic-activated or magnetic-responsive hydrogels, such as is discussed by Ilic-Stojanovic et al., *Stimuli-Sensitive Hydrogels for Pharmaceutical and Medical Applications*, Physics, Chemistry and Technology, Vol. 9, No. 1, pp. 37-56 (2011), which is incorporated herein by reference in its entirety.

The antenna 162, the EM generator 166, and a controller 240 are now described in greater detail.

The antenna 162 is used to radiate EM radiation into the tissue of the patient. The antenna 162 may be used in combination with a deflector or shield, that may ensure that the EM radiation radiated or emitted from the antenna 162 is radiated in the direction of the tissue of the patient exclusively or substantially (i.e., 80%, 90%, 95%, 98% or 99% of the radiation radiated is directed into the patient's tissue). The deflector or shield may ensure that the EM radiation is directed exclusively or substantially in the direction of the patient's tissue by redirecting the EM radiation toward the patient's tissue, or by absorbing that portion of the EM radiation radiated in directions other than in the direction of the patient's tissue. The antenna 162 may be tuned for EM radiation with a carrier frequency of 27±0.5 MHz, for example, with an available power of less than 1 mW and peak available radiated power density of less than 100 microwatts per cm$^2$.

The antenna 162 may be embedded in the base 152 or may be disposed on the base 152 (e.g. on the proximal side 180 or the distal side 182). If not embedded in the base 152, the antenna 162 (as well as the EM generator 166 and/or controller 240) may be enclosed in a housing or encapsulated in a protective layer to limit access to (and potential damage to) the antenna 162 (and the EM generator 166 and/or controller 240). The housing or protective layer may limit exposure to particulate matter (e.g., dust), fluids (e.g., water or water vapor), EM radiation (e.g., ultraviolet light), heat, and/or physical or mechanical shock.

The antenna 162 is not limited to a particular shape, and may include one or more conductors that do not make electrical contact with each other. According to certain embodiments, the antenna 162 may include conductors having a thickness of approximately 5 mm or less, and a length of less than approximately 27 cm. As illustrated above, the antenna 162 may be disposed within the array 190 or about the delivery device assembly 106, but this is merely by way of example and not by way of limitation.

The EM generator 166 may include an oscillator, a driver and a tuning coil, and may be coupled to the controller 240 (which may be in the form of, e.g., logic circuitry, a programmable logic device, or a microprocessor). The oscillator generates the EM field, the driver amplifies the EM field, and the tuning coil matches the impedance of the driver to the antenna 162. The controller 240 can be assembled or programmed to enable or disable the EM generator, and even may be assembled or programmed to create a pulse EM field (as opposed to a continuous EM field). A pulsed EM field may limit the heating of the tissue exposed to the EM field, and the pulses may be on the order of approximately 100 microseconds at intervals of approximately 1 millisecond.

The drug delivery device 150 will also include a power source or power supply to provide electrical power. According to certain embodiments, the power source may include one or more batteries. According to other embodiments, a radio-frequency circuit may be used to create an electric current that is used to power the electrical components of the drug delivery device 150. The drug delivery device 150 also may include a converter that is coupled between the power source and the other components (e.g., the EM generator 166 and the controller 240). The converter may boost and regulate the power source power level.

The controller 240 may operate the EM generator 166 to cause the antenna 162 to broadcast at one or more than one frequency (e.g., in a frequency range of 3 to 30 MHz). Along similar lines, the controller 240 may operated the EM generator 166 to cause the antenna 162 to broadcast one or more than one frequency range or one or more than one bandwidth. Further, the EM generator 166 may cause the antenna 166 to broadcast an EM field that has a changing orientation.

The controller 240 may have multiple states wherein, for example, the controller 240 causes the EM generator 166 to change between two or more different frequencies, frequency ranges, or bandwidths. The controller 240 may also control the EM generator to provide a field of particular frequency, power and duration, or to vary between fields of different frequency, power or duration.

According to certain embodiments, the controller 240 may be coupled to or include a radio-frequency (RF) receiver 242. The controller 240 may change from the first state to the second state upon receipt of an RF signal by the receiver 242.

In various embodiments, the device can be a combination product which further comprises a therapeutic or medicament. In the combination product, the therapeutic or medicament can be contained within a reservoir.

Exemplary drugs or pharmaceutical products to be contained with the reservoir are now discussed, with the caveat that the following list should neither be considered to be all inclusive nor limiting.

For example, the reservoir may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689;

and PCT Publ. Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publ. Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; US Publ. Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publ. Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publ. No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO: 2 as set forth therein in FIG. 2 and/or the heavy chain of SEQ ID NO:4, as set forth therein in FIG. 4, each of which is individually and specifically incorporated by reference herein in its entirety fully as disclosed in the foregoing Publication;

Myostatin binding proteins, peptibodies, and related proteins, and the like, including myostatin specific peptibodies, particularly those described in US Publ. No. 2004/0181033 and PCT Publ. No. WO 2004/058988, which are incorporated by reference herein in their entirety particularly in parts pertinent to myostatin specific peptibodies, including but not limited to peptibodies of the mTN8-19 family, including those of SEQ ID NOS: 305-351, including TN8-19-1 through TN8-19-40, TN8-19 con1 and TN8-19 con2; peptibodies of the mL2 family of SEQ ID NOS: 357-383; the mL15 family of SEQ ID NOS: 384-409; the mL17 family of SEQ ID NOS: 410-438; the mL20 family of SEQ ID NOS: 439-446; the mL21 family of SEQ ID NOS: 447-452; the mL24 family of SEQ ID NOS: 453-454; and those of SEQ ID NOS: 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publ. No. WO 2005/047331 or PCT Appl. No. PCT/US2004/37242 and in US Publ. No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publ. No. 2004/097712A1, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned U.S. publication;

Ang2 specific antibodies, peptibodies, and related proteins, and the like, including but not limited to those described in PCT Publ. No. WO 03/057134 and U.S. Publ No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publ. No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; Ab1F; Ab1K, Ab1P; and Ab1P, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in US Publ. No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publ. No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing International Publication;

Also among non-limiting examples of anti-IGF-1R antibodies for use in the methods and compositions of the present invention are each and all of those described in:

(i) US Publ. No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publ. No. WO 06/138729 (published Dec. 28, 2006) and WO 05/016970 (published Feb. 24, 2005), and Lu et al., 2004, J Biol. Chem. 279:2856-65, including but not limited to antibodies 2F8, A12, and IMC-A12 as described therein;

(iii) PCT Publ. No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) US Publ. No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) US Publ. Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al., 2003, Cancer Res. 63:5073-83, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), US Publ. Nos. 2005/0244408 (published Nov. 30, 2005) and 2004/0086503 (published May 6, 2004), and Cohen, et al., 2005, Clinical Cancer Res. 11:2063-73, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) US Publ. Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) US Publ. No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publ. No. 2008/0166352 and PCT Publ. No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing U.S. Publication;

IL-15 specific antibodies, peptibodies, and related proteins, and the like, such as, in particular, humanized monoclonal antibodies, particularly antibodies such as those disclosed in U.S. Publ. Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in US Publ. No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing US Publication and in Thakur et al., Mol. Immunol. 36:1107-1115 (1999). In addition, description of the properties of these antibodies provided in the foregoing US publication is also incorporated by reference herein in its entirety. Specific antibodies include those having the heavy chain of SEQ ID NO: 17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing US Publication. A specific antibody contemplated is antibody 1119 as disclosed in foregoing US Publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publ. Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing US Publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in US Publ. No. 2005/0118643 and PCT Publ. No. WO 2005/017107, huL2G7 described in U.S. Pat. No. 7,220,410 and OA-5d5 described in U.S. Pat. Nos. 5,686,292 and 6,468,529 and in PCT Publ. No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in US Publ. No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and US Publ. No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publ. No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO: 8 and a light chain variable region having SEQ ID NO: 6 as disclosed in the International Publication;

c-Kit specific antibodies, peptibodies, related proteins, and the like, including but not limited to those described in Publ. No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. application Ser. No. 11/086,289, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP 1Ib/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Ser. No. 13/469,032, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al., 2013, World Journal of Gastroenterology, 19:5138-5143); G207, 1716; NV1020; NV12023; NV1034 and NV1042 (Vargehes et al. 2002, Cancer Gene Ther, 2002, 9 (12): 967-978).

Also included are TIMPs. TIMPs are endogenous tissue inhibitors of metalloproteinases (TIMPs) and are important in many natural process. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. 61/782,613, U.S. 61/798,160, U.S. 61/802,988, and U.S. 61/940,67.

Also included are antagonistic antibodies for human calcitonin gene-related peptide (CGRP) receptor and bispecific antibody molecule that target the CGRP receptor and other headache targets. Further information concerning these molecule can be found in WO2A075238A1.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT/2013/075773.

Although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should also be understood that, unless a term is expressly defined in this patent using the sentence "As used herein, the term '_________' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

We claim:

1. A drug delivery device comprising:
    a base having a first region and a second region adjacent to the first region;
    a drug delivery assembly carried by the first region of the base for facilitating the delivery of a medicament to a patient during use of the drug delivery device, the drug delivery assembly including a plurality of needles disposed on the base;
    an antenna disposed in the first region of the base and at least partially between at least two of the plurality of needles; and
    an electromagnetic field generator carried by the base and in selective electrical communication with the antenna for selectively radiating an electromagnetic field from the antenna at least in a direction directly away from the base and into a tissue of the patient during use of the drug delivery device, thereby facilitating transfer of the medicament to the patient.

2. The drug delivery device according to claim 1, wherein the needles are microneedles having a first end attached to the base and a second end spaced therefrom and the antenna disposed adjacent to the plurality of microneedles.

3. The drug delivery device according to claim 1, wherein the drug delivery assembly comprises the medicament.

4. The drug delivery device of claim 2, wherein the plurality of microneedles defines an array of microneedles, and the antenna is disposed in a pattern adjacent to the array of microneedles.

5. The drug delivery device of claim 4, wherein the antenna is disposed in a serpentine pattern adjacent to the array of microneedles.

6. The drug delivery device of claim 2, further comprising a layer of antimicrobial agent disposed on the outer surface of the microneedles.

7. The drug delivery device of claim 2, wherein each microneedle has a longitudinal axis between the first and second ends, and the longitudinal axes of the microneedles are disposed at an angle to the plane of the base.

8. The drug delivery device of claim 7, wherein the angle is between approximately 15 degrees and approximately 90 degrees.

9. The drug delivery device of claim 8, wherein the angle is between approximately 15 degrees and approximately 45 degrees.

10. The drug delivery device of claim 9, wherein the angle is 30 degrees.

11. The drug delivery device of claim 2, wherein the each of the microneedles has a tear-drop cross-section in a plane parallel to the base.

12. The drug delivery device of claim 1, further comprising a controller coupled to the electromagnetic field generator and having a first state wherein the antenna is decoupled from the electromagnetic field generator and a second state wherein the controller couples the electromagnetic field generator to the antenna.

13. A method of delivering a drug to a patient comprising:
    applying a drug delivery device to a patient,
    the delivery device comprising a base having a first region with a drug delivery assembly associated therewith, the drug delivery assembly including a plurality of needles carried by the base, and an antenna disposed in the first region and at least partially between at least two of the plurality of needles to radiate an electromagnetic field, the base defining a plane and the antenna disposed in the plane of the base;
    emitting an electromagnetic field using the antenna, the electromagnetic field radiating directly away from the base and into a tissue of the patient adjacent to the drug delivery device, the electromagnetic field for causing migration of cells within the tissue of the patient; and
    delivering a drug to the patient via the drug delivery assembly, the drug being delivered to the tissue of the patient exposed to the electromagnetic radiation.

14. The method according to claim 13, wherein delivering the drug comprises delivering the drug to the patient through the plurality of needles, wherein the needles are microneedles carried by the base of the drug delivery device, the microneedles having a first end attached to a base of the drug delivery device and a second end spaced therefrom, the antenna disposed adjacent to the plurality of microneedles.

15. A drug delivery device comprising:
    a base having a first region and a second region with adhesive disposed thereon, the first region disposed within a plane defined by the base;
    a plurality of microneedles, each microneedle having a conical wall with a first end attached to the base and a second end spaced from the base and defining an opening, and an inner surface and an outer surface, the inner surface defining a needle reservoir in communication with the opening;

an antenna disposed in the first region of the base and adjacent to the first end of at least one of the plurality of microneedles; and an electromagnetic field generator carried by the base and in electrical communication with the antenna, the antenna radiating an electromagnetic field that is generated by the electromagnetic field generator at least in a direction directly away from the base during use of the drug delivery device;

wherein the antenna is at least partially between at least two of the plurality of microneedles.

16. The drug delivery device of claim 15, wherein the plurality of microneedles defines an array of microneedles, and the antenna is disposed in a pattern adjacent to the array of microneedles.

17. The drug delivery device of claim 16, wherein the antenna is disposed in a serpentine pattern adjacent to the array of microneedles.

18. The drug delivery device of claim 15, further comprising a controller coupled to the electromagnetic field generator and having a first state wherein the antenna is decoupled from the electromagnetic field generator and a second state wherein the controller couples the electromagnetic field generator to the antenna.

19. The drug delivery device of claim 1, further comprising a container and a volume of the medicament in the container, the medicament comprising a monoclonal antibody (IgG) that binds human Proprotein Convertase Subtilisin/Kexin Type 9 (PCSK9).

20. The drug delivery device of claim 15, further comprising a container and a volume of a medicament in the container, the medicament comprising a monoclonal antibody (IgG) that binds human Proprotein Convertase Subtilisin/Kexin Type 9 (PCSK9).

21. The drug delivery device of claim 1, further comprising a container and a volume of the medicament in the container, the medicament comprising a granulocyte colony-stimulating factor (G-CSF).

22. The drug delivery device of claim 15, further comprising a container and a volume of a medicament in the container, the medicament comprising a granulocyte colony-stimulating factor (G-CSF).

23. The method of claim 13, wherein delivering the drug comprises delivering a monoclonal antibody (IgG) that binds human Proprotein Convertase Subtilisin/Kexin Type 9 (PCSK9).

24. The method of claim 13, wherein delivering the drug comprises delivering a granulocyte colony-stimulating factor (G-CSF).

* * * * *